United States Patent [19]

Longino et al.

[11] Patent Number: 4,990,334

[45] Date of Patent: Feb. 5, 1991

[54] GLYCEROL-CHLORINE MATRIX

[76] Inventors: Ronald M. Longino, 2801 S. King Dr., #1902, Chicago, 60616; Elliott A. Treadwell, 1306 Naperville Rd., Wheaton, 60187; Dwight C. Boykins, 29 W. 431 Hawthorne, Warrenville, 60555, all of Ill.

[21] Appl. No.: 268,554

[22] Filed: Nov. 8, 1988

[51] Int. Cl.$^5$ .................................. A61K 9/08
[52] U.S. Cl. .................................. 424/401; 252/106; 252/187.26; 422/37; 424/402; 424/404; 424/405; 424/443; 424/661; 424/665
[58] Field of Search .............. 424/661, 665, 401, 405, 424/402, 404, 443; 422/37; 252/106, 187.26

[56] References Cited

U.S. PATENT DOCUMENTS

| | | | |
|---|---|---|---|
| Re. 31,779 | 12/1984 | Alliger | 424/665 X |
| 2,263,948 | 11/1941 | Halvorson et al. | 424/665 X |
| 2,840,080 | 6/1958 | Clark | 128/296 |
| 2,987,435 | 6/1961 | Davies et al. | 167/18 |
| 2,999,265 | 9/1961 | Duane et al. | 15/506 |
| 3,286,435 | 11/1966 | Weinberger | 53/64 |
| 3,363,625 | 1/1968 | Jovis | 128/260 |
| 3,414,927 | 12/1968 | Worcester | 15/104.93 |
| 3,542,634 | 11/1970 | Such et al. | 161/88 |
| 3,563,371 | 2/1971 | Heinz | 206/46 |
| 3,950,554 | 4/1976 | Prince | 424/665 X |
| 4,084,747 | 4/1978 | Alliger | 239/4 |
| 4,131,195 | 12/1978 | Worrell, Sr. | 206/205 |
| 4,428,477 | 1/1984 | Cristofolo | 206/210 |
| 4,557,381 | 12/1985 | Whitney | 206/440 |
| 4,575,891 | 3/1986 | Valente | 15/104.93 |
| 4,594,239 | 6/1986 | Pluim, Jr. | 424/10 |
| 4,690,772 | 9/1987 | Tell et al. | 424/665 X |
| 4,690,821 | 9/1987 | Smith et al. | 424/401 |
| 4,790,950 | 12/1988 | Hutchings | 424/665 X |

FOREIGN PATENT DOCUMENTS

| | | | |
|---|---|---|---|
| 0965699 | 4/1975 | Canada | 424/665 |
| 49-069822 | 7/1974 | Japan | 424/665 |
| 1367067 | 9/1974 | United Kingdom | 424/665 |

*Primary Examiner*—Thurman K. Page
*Attorney, Agent, or Firm*—Lee, Mann, Smith McWilliams & Sweeney

[57] ABSTRACT

The present invention is a germicidal solution for sanitizing the human epidermis without irritation. The solution is a homogenous blend of glycerol, sodium hypochlorite, inert ingredients, soft water, scented oil, and isopropyl alchol, having a pH of 9.8 to about 10.1. The solution may be applied to a towelette and sealed in a hermetically sealed pouch for later use.

15 Claims, No Drawings

GLYCEROL-CHLORINE MATRIX

BACKGROUND OF THE INVENTION

This invention relates to the germicidal efficiency of chlorine and compounds thereof in the presence of an alkaline pH and particularly relates to a highly alkaline germicidal solution applicable to the human epidermis without causing irritation.

We have discovered that maintaining an alkaline pH in a matrix of isopropyl alcohol (IPA), glycerol, sodium hypochlorite (NaOCl), inert ingredients, soft water and, preferably a scented oil with surfactant, will afford an increased germicidal formulation. It has also been found that embodying this formulation in a convenient pocket-sized towelette will provide the accessibility needed in a mobile society during travel, and participation in outdoor activities. There is an ever growing need for an effective, economical and convenient method of sanitation. In times of natural disasters, where water may not be available for use in cleansing hands and for surface decontamination, this invention may be employed for immediate sanitation. Custodians who are responsible for sanitary conditions in public places, such as school cafeterias and public washrooms, and other sanitation concerns encountered by civil workers (police and fire departments), embalmers, and health care workers, would all find application of our formulation beneficial for minimizing the risk of contamination from microorganisms. This formulation lends itself well for sanitizing skin prior to venipunctures and indwelling catheters.

Chlorine compounds are favorite ingredients in chemical compositions which clean, sanitize and disinfect surfaces. Previous sanitizing products which use chlorine compounds have been described in U.S. Pat. Nos.: 2,987,435, issued to Thomas Gwyn Davies et al.; 2,999,265, issued to Jerome J. Duane et al.; 3,363,625, issued to Arthur Jovis; 4,084,747, issued to Howard Alliger; 4,594,239, issued to Pluim, Jr.; and 4,690,821, issued to James A. Smith, et al. One compound, sodium hypochlorite is the best oxidizing member of the chlorite group and was used by health workers during World War I to irrigate and sanitize wounds.

The Smith et al. patent, is a towel for skin moisturizing and drying. It is a cosmetic application with emollient oils of both hydrophillic and hydrophobic properties. The pH range is neutral 6.0 to 7.5 and the germicide is 0.01 to 5.0% chlorohexadiene gluconate, a salt or ester of a gluconic acid. This cosmetic should remain chemically stable under normal room temperature and atmospheric pressure.

The glycerol-chlorine solution of our invention uses sodium hypochlorite, preferably at 1.0% to 2.1% by weight or 0.5% to 1.0% available chlorine. Sodium hypochlorite has the highest oxidizing strength of all chlorine compounds and the glycerol-chlorine solution has more available chlorine for a given concentration of sodium hypochlorite than the chlorohexadiene gluconate salt does at the same concentration. In addition the chlorohexadiene gluconate may decompose into lower mass chlorine compounds which are either chemically inactive or active within a narrow pH range.

The Pluim, Jr. patent is a method for neutralizing offensive chemicals, e.g., uroshiol, in contact with wearing apparel. An application of the Pluim, Jr. composition decontaminates the surface and neutralizes the uroshiol with a chlorine compound solution. The composition has acetone, alcohols, and the following chlorine compounds: N-chloramine liquid 0.5%–5.0% by weight, chloramine-B, chloramine-T, chloroisocyanurics, chlorinated hydantoins, N-chlorosuccinimide, trichloroisocyanuric, ferric chloride, 1,3-dichloro-5, 5-dimethyl hydantoin, and trichloromelamines.

Each chlorine compound in the Pluim, Jr. patent has less available chlorine in the solution than is found in the same amount of sodium hypochlorite. Therefore Pluim, Jr. combines ten chlorine compounds into a stable, alkaline solution in order to increase the germicidal properties. There is no application of this composition to human epidermal tissue.

The Alliger patent claims a process for the production of a germ killing composition. The chlorine compound is sodium chlorite, and the solution includes lactic acid and water. Lactic acid, which is 15% by weight of the solution, is used to maintain a pH of 7.0. The compound is in contact with an ultrasonic cleaner or dispensed in a pressurized aerosol.

Sodium chlorite is an explosive compound and is not to be handled by the inexperienced. It has a lower oxidizing strength than sodium hypochlorite and releases less chlorine in the solution. Alliger does not teach the use of this composition on human tissue. The use of organic and inorganic acids in the composition complicates the matrix of chemical possibilities. The composition should be stable over a wide range of pressure.

The Jovis patent discloses a medicinal applicator with an envelope element and a pad element. The cleansing agents are hexachlorophene, boric acid or resorcinol; and the emollients are glycerine, lanolin and carbonated pertroleum jelly. The chlorine compound hexachlorophene is a powdered phenolic, i.e. an acidic compound, bacteria inhibiting agent. The amount of available chlorine in the solution of hexachlorophene is less than the chlorine found in the same amount of sodium hypochlorite. Hydrocarbons in a composition increase the reaction possibilities for chlorine. Most of these organic compounds have low germicidal properties and become inert.

The Duane et al. patent provides a saturated pad for cleansing and deodorizing the female pelvic region. The pH range is 5.0 to 6.5 and the bacteriostatic agent, which is 0.1% to 2.0% by weight, has the chlorine compounds hexachlorophene, trichlorophenol, and 4-chloro-3,5-xylenol.

The chlorine compounds in the Duane et al. patent are organic acids with a complex chemical matrix. This patent does not discuss how much of the available chlorine reacts with hydrocarbons to form chloramines and chemically inactive compounds in the composition. Chloramines are stable compounds which release chlorine within limited pH windows, e.g. 5.0 to 6.5

The Davies et al. patent is directed to germicidal compositions for cleaning and disinfecting materials. One composition has sodium hypochlorie (0.45% to 5.0%) available chlorine with an aqueous solution of benzalkonium chloride (0.5% to 5.0%) by weight. Another germicidal composition has sodium hypochlorite and cetyl trimethyl ammonium bromide, both in equal amounts. The compositions are alkaline with ionic salts added to the sodium hypochlorite solutions; and stable if handled under normal room temperature and atmospheric pressure.

The Davies et al. patent provides germicidal compositions for cleaning materials with keratinous fibers and celluosic fibers. The Davies et al. compositions are alkaline and can cause caustic irritations to human skin. The ammonium and organic salts and sodium hypochlorite produce a complex matrix of chemical reactions, which include the formation of chloramines and chemically inactive chlorine compounds.

SUMMARY OF THE INVENTION

Our invention is a germicidal solution, preferably scented, comprising a glycerol-chlorine matrix. The solution is a blend of six ingredients: sodium hypochlorite, glycerol, soft water, isopropyl alcohol, inert ingredients and scented fragrance (oil) with a surfactant. The possible chemical reactions within the solution have been analyzed and the results have been represented in matrix form in the following. Our glycerol-chlorine matrix is a highly effective sanitizing solution on human epidermis, without irritation.

DETAILED DESCRIPTION OF THE INVENTION

The invention glycerol-chlorine solution is a complex medium of six components: glycerol; an aqueous solution of sodium hypochlorite; inerts in the sodium hypochlorite solution; soft water; fragrant oil; and isopropyl alcohol (IPA) which is over 99.0% pure IPA. A deciliter exemplary formulation of the glycerol-chlorine matrix is set forth in Table 1. Each compound in the matrix is listed according to chemical name, weight (grams), fraction of the solution weight (%), solute density (grams/milliliters), and volume (milliliters). The optimal formulation is set out with the effective range (+/−) following. There is no anhydrous form of sodium hypochlorite and therefore the mixture has sodium, hypochlorous, and hydroxyl ions in a water solution.

TABLE 1

Exemplary Formulation Of The Glycerol-Chlorine Matrix (Scented)

| Chemical Name | Weight (g) | Percentage By Weight (Optimal & Range) | Density (g/ml) | Volume (ml) |
|---|---|---|---|---|
| GLYCEROL | 3.00 | 3.2+/−1.8% | 1.0051 | 2.98 |
| SODIUM HYPOCHLORITE | 2.00 | 2.1+/−1.0% | 1.2440 | 1.61 |
| INERTS IN THE SODIUM HYPOCHLORITE MIX | 11.28 | 12.0+/−1.0% | 1.2393 | 9.10 |
| SOFT WATER | 45.84 | 48.8+/−3.0% | 1.0000 | 45.77 |
| OIL FRAGRANCE (W/SURFACTANT) | 0.50 | 0.5+/−0.4% | 0.9200 | 0.54 |
| ISOPROPYL ALCOHOL | 31.40 | 33.4+/−3.0% | 0.7851 | 40.00 |

The following physical constraints have limited the use of sodium hypochlorite in sanitizing products: a) sodium hypochlorite reacts with the water solution and releases chlorine gas. This loss of chlorine gas lowers the concentration of chlorine ions in solution, steps the oxidation of microbial cells, and increases the concentration of sodium hydroxide; b) the sodium hypochlorite solution is alkaline and may bleach surfaces on contact or leave caustic burns on human epidermis. Therefore, over the years, those skilled in the art have avoided the use of sodium hypochlorite and have developed a class of compounds called chloramines (e.g., $NH_2Cl$). Chloramines combine the oxidizing attributes of the chlorites and ammonium salts.

Consider the following reactions which depend upon sodium hypochlorite and water:

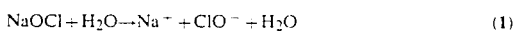

$$NaOCl + H_2O \rightarrow Na^+ + ClO^- + H_2O \qquad (1)$$

$$ClO^- + H_2O \rightleftharpoons HClO + OH^- \qquad (2)$$

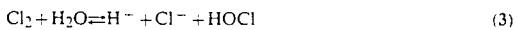

$$Cl_2 + H_2O \rightleftharpoons H^+ + Cl^- + HOCl \qquad (3)$$

Reaction (1) demonstrates the dependence of sodium hypochlorite on the water solution. The hypochlorous ions dissociate from the sodium ions and become mobile in water. Hypochlorous ions in reaction (2) form a chemical equilibrium with hypochlorous acid and hydroxyl ions. The hypochlorous acid in reaction (3) then forms a chemical equilibrium with molecules of chlorine gas. If chlorine gas escapes, the concentration of hypochlorous and chlorine ions decreases and the solution no longer has its germicidal properties.

We have corrected the gas problem with the formulation of our glycerol-chlorine matrix. The hypochlorous acid in reaction (3) is neutralized by sodium hydroxide present in solution:

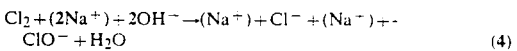

$$Cl_2 + (2Na^+) + 2OH^- \rightarrow (Na^+) + Cl^- + (Na^+) + ClO^- + H_2O \qquad (4)$$

Chlorine remains in solution with hypochlorous ions and does not escape like the gas in reaction (3).

Glycerol ($C_3H_8O_3$) is a hygroscopic trihydroxy alcohol which retains moisture when it is applied to epidermal surfaces. Combining glycerol with the drying compound, isopropyl alcohol, human skin is left "looking moist" and feeling dry. Glycerol is optimally present at 3.2% by weight and isopropyl alcohol optimally present at 33.4% by weight of the matrix. The effective range of the glycerol content is +/−1.8%. This is an effective range for the glycerol to attract water without forming globules. The isopropyl alcohol content is +/−3.0%. Higher than this range usually results in an overpowering smell which is subjectively undesirable. Both solvents are used to dissolve oils. Acetone is usually present in isopropyl alcohol when the alcohols are oxidized. The presence of acetone is undesirable. Firstly, it may be harmful to the skin and, secondly, people with diabetes are particularly concerned about materials that might include acetone due to the need to prevent ketones from being introduced to the blood. It is therefore important to minimize the risk of acetone and therefore a 99.0% pure, reagent quality, IPA is used in the optimal formulation of Table 1. With less pure IPA there is an increase in the breakdown to acetone and water. A common test device for detecting the presence of acetone is a column gas chromatograph. We have tested for acetone in the solution made pursuant to the Table 1 formulation with a water stable column gas chromatograph. One microliter injections of the solution into the column show no acetone. When a 70% pure IPA was tested, a 2% contaminated acetone level was detected. With a 99.0% pure IPA, the acetone level is undetectable. When pure, reagent quality products are used in the matrix formulation the risk of contamination is minimal. For this safe reason 99.0% pure IPA should be used.

One oil usable in the matrix solution is Lemon Fragrance #5309, which is an Environmental Protection Agency (EPA) certified product of Orchid Laboratories (Downers Grove, Ill.). The lemon oil produces a subtle scent which masks the IPA odor and is uniformly distributed throughout the solution. Other lemon fragrances (with surfactants) identified under code numbers 1285, 1800 and 5309, and lemon oils having code numbers 1122-1 and 113N, are suitable alternatives made by Orchid Laboratories. Other equivalent oil extracts and fragrances that are EPA certified may be substituted as one skilled in the art would understand. The purpose of the fragrance in the glycerol-chlorine matrix is subjective in order to mask the odor of the IPA which consumers might find objectionable. The glycerol-chlorine matrix is effective without the fragrance. In that alternative, the isopropyl alcohol would be at the upper end of its range to aid in emulsifying any oils present to dissolve them in the water. Fragrant oils, such as Lemon Fragrance #5309 of the preferred embodiment, include a surfactant to emulsify the oil for dissolving it in the water. Accordingly, utilization of a fragrant oil requires the provision of a surfactant or emollient. The surfactant provided with Lemon Fragrance #5309 is identified as being made by Texaco Co. and sold under the brand name SURFONIC J4. It is an alkoxypolyalkoxy-ethanol, nonionic surface-active agent which is stable up to 190.6° C. and is biodegradable. Other equivalent surfactants may by substituted and are preferably bio-degradable. Surfactants that are used as agents in detergents to break down the oils may be useful. Some alternatives for use in the present invention are: POLY-TERGENT made by Olin Corp. (code number SL-62); PLURAFAC made by BASF Corp.—Wyandotte (Chemical Division) (code number B26-D-25); BIO-SOFT made by Stepan Chemical Co. (code number EA-10); and, TERGITOL made by Union Carbide (code number 15-S-9).

The Matrix of Possible Chemical Combinations

There are twelve fundamental chemical ingredients in the glycerolchlorine solution which define its chemically active and passive properties. The fundamental ingredients are 1) glycerol, 2) sodium ions from the soft water and sodium hypochlorite solution, 3) water, 4) oxygen gas molecules, 5) hydroxyl ions, 6) hypochlorous ions, 7) the surfactant for the oil fragrance (e.g. Surfonic J4), 8) the oil fragrance (e.g. Lemon Fragrance #5309), 9) isopropyl alcohol, 10) chlorine gas molecules, 11) chlorine ions, and 12) hydrogen ions (protons).

It is convenient to represent the array of chemical possibilities in a matrix form. The glycerol-chlorine matrix of the present invention has twelve rows and twelve columns, or a dimensional space of 144 pairs. Each pair represents a possible chemical state of two ingredients in the solution. Table 1A is a matrix of the 144 possible chemical pairs. The lower portion of the matrix, i.e., 78 pairs, are zeroed since pairs should not be redundant, for example, glycerol and glycerol, or glycerol and IPA in addition to IPA and glycerol. All 66 pairs which are nonzero define the set of chemical possibilities in the glycerol-chlorine solution.

The effectiveness of using a matrix representation is that it makes it possible to isolate the chemically active pairs or germicidal agents of the solution from the chemically passive pairs. When we impose the criterion that at least one member of each pair should have the potential to oxidize microbes we obtain the set of 38 pairs in Table 1B. Each column has the upper member of the pair repeated in combination with another ingredient. Each row has the lower member of the pair repeated in combination with another ingredient. It is noteworthy to identify a few pairs which could otherwise form chemically inactive chlorine compounds, e.g. sodium chloride and isopropyl chloride, or compositions which are harmful to the skin, e.g. hydrochloric acid, chlorite ions, and sodium hydroxide. These compositions are undetectable in the glycerolchlorine matrix, either because of their low concentration or that the pairs form ions instead of compounds in an aqueous solution.

A Key To The Matrix Of Possible Chemical Combinations In The Glycerol-Chlorine Solution

| ORDER | SYMBOL | DESCRIPTION |
|---|---|---|
| 1. | GLY | Glycerol ($C_3H_8O_3$) |
| 2. | $Na^+$ | Sodium Ion |
| 3. | $H_2O$ | Water Molecule |
| 4. | $O_2$ | Oxygen Gas Molecule |
| 5. | $OH^-$ | Hydroxyl Ion |
| 6. | $ClO^-$ | Hypochlorous Ion |
| 7. | SJ4 | Surfactant Surfonic J4 |
| 8. | L5309 | Lemon Fragrance 5309 |
| 9. | IPA | Isopropyl Alcohol |
| 10. | $Cl_2$ | Chlorine Gas Molecule |
| 11. | $Cl^-$ | Chlorine Ion |
| 12. | $H^+$ | Hydrogen Ion (Proton) |

TABLE 1A

The Glycerol-Chlorine Matrix of Chemical Pairs

| 0 | $Na+$ | $H_2O$ | $O_2$ | $OH-$ | $ClO-$ | SJ4 | L5309 | IPA | $Cl_2$ | $Cl-$ | $H+$ |
|---|---|---|---|---|---|---|---|---|---|---|---|
|   | Gly | Gly | Gly | Gly | Gly | Gly | Gly | Gly | Gly | Gly | Gly |
| 0 | 0 | $H_2O$ | $O_2$ | $OH-$ | $ClO-$ | SJ4 | L5309 | IPA | $Cl_2$ | $Cl-$ | $H+$ |
|   |   | $Na+$ | $Na+$ | $Na+$ | $Na+$ | $Na+$ | $Na+$ | $Na+$ | $Na+$ | $Na+$ | $Na+$ |
| 0 | 0 | 0 | $O_2$ | $OH-$ | $ClO-$ | SJ4 | L5309 | IPA | $Cl_2$ | $Cl-$ | $H+$ |
|   |   |   | $H_2O$ | $H_2O$ | $H_2O$ | $H_2O$ | $H_2O$ | $H_2O$ | $H_2O$ | $H_2O$ | $H_2O$ |
| 0 | 0 | 0 | 0 | $OH-$ | $ClO-$ | SJ4 | L5309 | IPA | $Cl_2$ | $Cl-$ | $H+$ |
|   |   |   |   | $O_2$ | $O_2$ | $O_2$ | $O_2$ | $O_2$ | $O_2$ | $O_2$ | $O_2$ |
| 0 | 0 | 0 | 0 | 0 | $ClO-$ | SJ4 | L5309 | IPA | $Cl_2$ | $Cl-$ | $H+$ |
|   |   |   |   |   | $OH-$ | $OH-$ | $OH-$ | $OH-$ | $OH-$ | $OH-$ | $OH-$ |
| 0 | 0 | 0 | 0 | 0 | 0 | SJ4 | L5309 | IPA | $Cl_2$ | $Cl-$ | $H+$ |
|   |   |   |   |   |   | $ClO-$ | $ClO-$ | $ClO-$ | $ClO-$ | $ClO-$ | $ClO-$ |
| 0 | 0 | 0 | 0 | 0 | 0 | 0 | L5309 | IPA | $Cl_2$ | $Cl-$ | $H+$ |
|   |   |   |   |   |   |   | SJ4 | SJ4 | SJ4 | SJ4 | SJ4 |
| 0 | 0 | 0 | 0 | 0 | 0 | 0 | 0 | IPA | $Cl_2$ | $Cl-$ | $H+$ |
|   |   |   |   |   |   |   |   | L5309 | L5309 | L5309 | L5309 |
| 0 | 0 | 0 | 0 | 0 | 0 | 0 | 0 | 0 | $Cl_2$ | $Cl-$ | $H+$ |
|   |   |   |   |   |   |   |   |   | IPA | IPA | IPA |
| 0 | 0 | 0 | 0 | 0 | 0 | 0 | 0 | 0 | 0 | $Cl-$ | $H+$ |
|   |   |   |   |   |   |   |   |   |   | $Cl_2$ | $Cl_2$ |

TABLE 1A-continued

| The Glycerol-Chlorine Matrix of Chemical Pairs | | | | | | | | | | | |
| --- | --- | --- | --- | --- | --- | --- | --- | --- | --- | --- | --- |
| 0 | 0 | 0 | 0 | 0 | 0 | 0 | 0 | 0 | 0 | 0 | H+ Cl− |
| 0 | 0 | 0 | 0 | 0 | 0 | 0 | 0 | 0 | 0 | 0 | 0 |

TABLE 1B

| The Glycerol—Chlorine Matrix Of Germicidal Pairs | | | | | | | |
| --- | --- | --- | --- | --- | --- | --- | --- |
| OH—Gly | ClO—Gly | | | IPA | | Cl—Gly | |
| OH—Na+ | ClO—Na+ | | | IPA Na+ | | Cl—Na+ | |
| OH—H$_2$O | ClO—H$_2$O | | | IPA H$_2$O | | Cl—H$_2$O | |
| OH—O$_2$ | ClO—O$_2$ | | | IPA O$_2$ | | Cl—O$_2$ | |
| | ClO—OH− | SJ4 OH− | L5309 OH− | IPA OH− | Cl$_2$ OH− | Cl—OH− | H+ OH− |
| | | SJ4 ClO− | L5309 ClO− | IPA ClO− | Cl$_2$ ClO− | Cl—ClO− | H+ ClO− |
| | | | | IPA SJ4 | | Cl- SJ4 | |
| | | | | IPA L5309 | | Cl- L5309 | |
| | | | | | Cl$_2$ IPA | Cl- IPA Cl—Cl$_2$ | H+ IPA |
| | | | | | | | H+ Cl− |

Physical Properties of the Matrix

The glycerol-chlorine matrix made pursuant to Table 1 is a clear yellow liquid. The solution is preferably maintained at the temperature range of from about 2.0° C. to about 20.0° C. The solution will begin to lose chlorine at temperatures in excess of about 20.0° C. Alcohol, water and oil vapors may escape until the sodium chloride remains.

One manner of utilizing our invention is to provide a towelette saturated with the solution within a hermetically sealed pouch. An example of such use would be to provide a convenient size paper polyfoil surlyn pouch or package in a convenient size of about 3 inches by 3 inches. The paper polyfoil surlyn material is generally manufactured in rolls and may be cut and heat sealed. A towelette formed of a non-woven rayon, cotton and polypropylene is also available in rolls. One alternative is spun-polypropylene. These materials may be formed into a pad from an unfolded 36 square inch sheet to a 2¾ inch × 2¾ inch pad. Then, the pad may be soaked for example with a 2.5 milliliter volume of the glycerol-chlorine matrix and heat sealed within the paper polyfoil surlyn formed into a pouch. Typically, these hermetically heat sealed pouches are clay coated for use with ink and an over-layer of lacquer. A towelette package according to this foregoing procedure was made and kept at a temperature from 16° C. to 20° C. for over sixty days. It effectively retained the germicidal properties. Thus, the invention in this form would meet all governmental health and shelf-life requirements for sanitizing products as one skilled in the art would understand.

A neutral pH range (6.0 to 7.5) is typically filled with salts and is the pH found in human blood and tissue. The glycerol-chlorine solution of our invention has a pH range of 9.8 to 10.1 and therefore is highly alkaline.

Microbes cannot live in highly alkaline solutions because of the bleaching agents chlorine and hypochlorous ions. The same ions are responsible for bleaching surfaces on contact, a major concern of previous inventors interested in applications to human epidermis. The perception of inventors in the prior art has been that no highly alkaline solution should be applied to human epidermal tissue. This perception has merit when one considers the present use of chlorine compounds in cleansing and sanitizing solutions; however our glycerol-chlorine matrix utilizes the hygroscopic properties of glycerol (preferably in an amount about 3.2% +/−1.8% of solution by weight) to attract water and oils to the point of contact. Molecular layers of glycerol, water, oils to the point of contact. Molecular layers of glycerol, water, oils, such as lemon oil, and IPA prohibit chlorine ions and compounds from irritating human skin. The film prevents bleaching with several molecular layers of oil and water coating the surface. The film remains germicidal since the solution has chlorine and hypochlorous ions; but is absorbed into the outer epidermis and evaporated approximately two seconds after application through the drying action of isopropyl alcohol.

Microcidal Studies with the Glycerol-Chlorine Matrix

Microcidal studies were conducted in the standard microbiological fashion and tabulated on the following Table 2. Agar plates were inoculated with a range of organisms known to be one of the primary etiological agents in opportunistic and non-opportunistic infections in humans. The organisms tested include Staphlococcus aureus, Staphlococcus epidermidis, Streptococcus faecalis (entrococci), Klebsiella pneumoniae, Esherichia coli, Pseudomanas aeruginosa, and a yeast, Candida albvicans. The bacterial organisms cited were selected on pathogenecity. Staphlococcus aureus is one of the organisms seen in food poisoning as well as topical dermatological infections. Also Staphlococcus epidermis has been cited in a large number of skin abscesses. Klebsiella pneumoniae is seen commonly in upper respiratory and in pediatric ear infections. Psuedomonas aeruginosa is widely cited in gastrointeritis. Esherichia coli has been isolated in a range of infections from skin to a number of subcutaneous inflammations. Finally, Candida albicans is reported to be one of the primary etiological agents in yeast vaginitis as well as urinary tract infections of the immunosuppressed population.

The method of study was to demonstrate that the uninoculated agar media was indeed sterile, while positive growth on the inoculated agar represented the uninterrupted growth of organisms. Agar media plates uninoculated were incubated at body temperature 37.0° C. for 24 hours, 48 hours, 72 hours, and 168 hours. They were observed at the above time intervals for contamination growth. This was the negative control. Agar plates were also inoculated with a previously mentioned organisms and incubated at 37.0° C. for 24 hours, 48 hours, 72 hours and 168 hours. The plates were observed for growth. This was the positive control (Table 2). Lastly, the test organisms were inoculated on agar plates then 1.0 of the formulation of Table 1 was applied to the center surface, given a radius of 2.0 cm. The plates were then incubated at 37.0° C. for 24 hours, 48 hours, 72 hours and 168 hours. The agar plates were observed at the above mentioned time intervals for bacterial growth. This was done to determine the duration of the germicidal activity of the glycerolchlorine matrix. The test results are illustrated by positive or negative symbols in Table 2.

tions were again conducted after 24 hours and no untoward effects were demonstrated.

TABLE 3

| Mice Epidermal Inoculation With Glycerol-Chlorine Matrix | | | | | |
|---|---|---|---|---|---|
| Mice: | Macula | Papules | Vesicles | Erythema | Irritation |
| White 1 | − | − | − | − | − |
| White 2 | − | − | − | − | − |
| White 3 | − | − | − | − | − |
| White 4 | − | − | − | − | − |
| White 5 | − | − | − | − | − |
| White 6 | − | − | − | − | − |
| White 7 | − | − | − | − | − |
| Brown 1 | − | − | − | − | − |
| Black 1 | − | − | − | − | − |
| Black 2 | − | − | − | − | − |

Key To Above Table 3
+ no positive reaction
− no reaction

Criteria For Human Studies With Glycerol-Chlorine Matrix

Human subjects were selected based upon hair color, skin color, eye color, age and sex. Subjects with a history of topical irritations were included in this test group. A 2.5 ml volume of the formulation of the solution pursuant to Table 1 was applied to a 36 square inch nonwoven ray, cotton and polypropylene material and

TABLE 2

| | Microcidal Effectiveness of Glycerol-Chlorine Matrix | | | | | | | | | |
|---|---|---|---|---|---|---|---|---|---|---|
| Organisms Tested | 24 Hr. Test | Pos. Con. | Neg. Con. | 48 Hr. Test | Pos. Con. | Neg. Con. | 72 hr. Test | Pos. Con. | Neg. Con. | 168 Hr. Test |
| Staph. aureus | − | + | − | − | + | − | − | + | − | − |
| Staph. epid. | − | + | − | − | + | − | − | + | − | − |
| Strep. face. | − | + | − | − | + | − | − | + | − | − |
| Kleb. pneu. | − | + | − | − | + | − | − | + | − | − |
| E. coli | − | + | − | − | + | − | − | + | − | − |
| Pseud. aerug. | − | + | − | − | + | − | − | + | − | − |
| Cand. albic. | − | + | − | − | + | − | − | + | − | − |

Key To Above Table 2
+ represents growth
− represents no growth

Mammal Epidermal Studies With Glycerol-Chlorine Matrix

Animal studies were conducted on ten laboratory mice of the Sprague species and tabulated on the following Table 3. Seven were white, two were black, and one brown. The animals were shaved and then their epidermal surfaces were inoculated with the glycerolchlorine matrix solution pursuant to the formulation of Table 1. Immediate observations were made for deleterious effects and none were observed. These observafolded into a $2\frac{3}{4}'' \times 2\frac{3}{4}''$ towelette. The coated towelette was frictionally applied to one side of the face and the palmer and dorsal surfaces of one hand. Isopropyl alcohol was used as a control on the other side of the face and on the other hand of the subjects. After one hour the subjects were observed with respect to the presence or absence of the irritation listed in the first four columns (Table 4). The fifth column labeled "Irritation" reflects whether any one or combination of the other reactions occurred. No positive reactions were evident and no oral reports of irritation were made by the subjects. The results of the studies are tabulated in Table 4.

TABLE 4

| Human Epidermal Studies With Glycerol-Chlorine Matrix | | | | | | | | | |
|---|---|---|---|---|---|---|---|---|---|
| | Human Characteristics | | | | | | | | |
| | Hair Color | Skin Color | Eye Color | Age Sex | Macula | Papules | Vesicles | Erythema | Irritation |
| 1. | Rd | Li | Blu | 40 yrs M | − | − | − | − | − |
| 2. | Br | Li | Br | 39 yrs F | − | − | − | − | − |
| 3. | Br | Li | Blu | 26 yrs F | − | − | − | − | − |

TABLE 4-continued

Human Epidermal Studies With Glycerol-Chlorine Matrix

| | Human Characteristics | | | | | | | | |
|---|---|---|---|---|---|---|---|---|---|
| | Hair Color | Skin Color | Eye Color | Age Sex | Macula | Papules | Vesicles | Erythema | Irritation |
| 4. | Bd | Li | Blu | 28 yrs M | — | — | — | — | — |
| 5. | Bk | Dk | Br | 33 yrs M | — | — | — | — | — |
| 6. | Br | Li | Blu | 39 yrs M | — | — | — | — | — |
| 7. | Bk | Li | Br | 24 yrs F | — | — | — | — | — |
| 8. | Br | Br | Br | 36 yrs M | — | — | — | — | — |
| 9. | Bk | Br | Br | 0.5 yrs F | — | — | — | — | — |
| 10. | Bd | Li | Blu | 5 yrs F | — | — | — | — | — |

Key To Above Table 4
Bd: Blond
Br: Brown
Bl: Black
Blu: Blue
Li: Light Complexion
Dk: Dark Complextion
Rd: Red
Yrs: Years
M: Males
F: Females
+: positive reaction
—: negative reaction Accordingly, a very useful and effective sanitizing solution has been provided which may be conveniently applied to a towelette and hermetically sealed in a packet for later use. One skilled in the art would understand that the foregoing exemplary embodiment of the invention is for purposes of disclosure and accordingly it is considered that the claims appended hereto have a wide range and scope of equivalents.

What is claimed is:

1. A germicidal solution comprising:
   (a) glycerol in the range of about 3.2% +/−1.8% by weight;
   (b) sodium hypochlorite in the range of about 2.1% +/−1.0% by weight;
   (c) soft water, including sodium ions, in the range of about 60.8% +/−3.0% by weight;
   (d) fragrant oil and non-ionic surfactant in the range of about 0.5% +/−0.4% by weight; and
   (e) isopropyl alcohol in the range of about 33.4% +/−3.0% by weight.

2. The solution of claim 1, wherein the oil comprises a fragrant lemon oil.

3. The solution of claim 2 wherein the surfactant is a surface-active agent.

4. The solution of claim 3 wherein the surfactant is an alkoxypolyalkoxy-ethanol.

5. An alkaline sanitizing solution having a pH no less than about 9.8 and comprising a matrix of isopropyl alcohol, glycerol, sodium hypochlorite, inert ingredients and soft water.

6. The solution of claim 1 wherein the pH is greater than 9.0.

7. The solution of claim 6, wherein said solution has a pH in the range of 9.8 to 10.1.

8. The solution of claim 1, wherein said isopropyl alcohol is 99.0 percent pure.

9. A method for sanitizing skin, comprising the step of applying an alkaline solution, including glycerol, isopropyl alcohol and sodium hypochlorite, to the skin in an amount to effectively sanitize the skin.

10. The sanitizing solution of claim 5 wherein the solution is germicidal.

11. The sanitizing solution of claim 5 wherein the isopropyl alcohol is 99.0 percent pure.

12. The sanitizing solution of claim 5 wherein the sodium hypochlorite is present in the range of from about 1.0 percent to about 2.1 percent by weight.

13. The sanitizing solution of claim 5 wherein the solution comprises sodium, chlorine, hypochlorous and hydroxyl ions in a water solution.

14. The sanitizing solution of claim 5 including a scented oil and surfactant.

15. The sanitizing solution of claim 14 wherein the surfactant is an alkoxypolyalkoxy-ethanol.

* * * * *